(12) United States Patent
Wang et al.

(10) Patent No.: US 7,740,580 B2
(45) Date of Patent: Jun. 22, 2010

(54) ANALYTE MONITORING

(75) Inventors: Yi Wang, San Ramon, CA (US); Steve Scott, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 334 days.

(21) Appl. No.: 11/555,146

(22) Filed: Oct. 31, 2006

(65) Prior Publication Data

US 2008/0119709 A1    May 22, 2008

(51) Int. Cl.
*A61B 5/00* (2006.01)
*C12Q 1/54* (2006.01)

(52) U.S. Cl. .................. 600/309; 600/365; 204/403.01; 435/14

(58) Field of Classification Search .................. 600/309, 600/345–347, 365
See application file for complete search history.

(56) References Cited

U.S. PATENT DOCUMENTS

| | | | |
|---|---|---|---|
| 4,545,382 A | 10/1985 | Higgins et al. | |
| 4,711,245 A | 12/1987 | Higgins et al. | |
| 4,774,192 A * | 9/1988 | Terminiello et al. | 436/530 |
| 5,279,294 A * | 1/1994 | Anderson et al. | 600/322 |
| 5,509,410 A | 4/1996 | Hill et al. | |
| 5,526,120 A | 6/1996 | Jina et al. | |
| 5,628,890 A | 5/1997 | Carter et al. | |
| 5,820,551 A | 10/1998 | Hill et al. | |
| 6,071,391 A | 6/2000 | Gotoh et al. | |
| 6,120,676 A | 9/2000 | Heller et al. | |
| 6,143,164 A | 11/2000 | Heller et al. | |
| 6,175,752 B1 | 1/2001 | Say et al. | |
| 6,183,274 B1 * | 2/2001 | Allum | 439/135 |
| 6,268,162 B1 * | 7/2001 | Phillips et al. | 435/14 |
| 6,299,757 B1 | 10/2001 | Feldman et al. | |
| 6,338,790 B1 | 1/2002 | Feldman et al. | |
| 6,377,894 B1 | 4/2002 | Deweese et al. | |
| 6,461,496 B1 | 10/2002 | Feldman et al. | |
| 6,503,381 B1 | 1/2003 | Gotoh et al. | |
| 6,506,168 B1 | 1/2003 | Fathallah et al. | |
| 6,514,460 B1 | 2/2003 | Fendrock | |
| 6,514,718 B2 | 2/2003 | Heller et al. | |
| 6,540,891 B1 | 4/2003 | Stewart et al. | |
| 6,591,125 B1 | 7/2003 | Buse et al. | |
| 6,592,745 B1 | 7/2003 | Feldman et al. | |
| 6,600,997 B2 | 7/2003 | Deweese et al. | |
| 6,616,819 B1 | 9/2003 | Liamos et al. | |
| 6,618,934 B1 | 9/2003 | Feldman et al. | |
| 6,676,816 B2 | 1/2004 | Mao et al. | |
| 6,730,200 B1 | 5/2004 | Stewart et al. | |
| 6,736,957 B1 | 5/2004 | Forrow et al. | |
| 6,749,740 B2 | 6/2004 | Liamos et al. | |
| 6,764,581 B1 | 7/2004 | Forrow et al. | |
| 6,773,671 B1 | 8/2004 | Lewis et al. | |

(Continued)

FOREIGN PATENT DOCUMENTS

EP    1112717 A1    7/2001

(Continued)

*Primary Examiner*—Patricia C Mallari
*Assistant Examiner*—Karen E Toth
(74) *Attorney, Agent, or Firm*—Edward J. Baba; Bozicevic, Field & Francis LLP

(57) ABSTRACT

Methods for covering an opening in an analyte meter are provided. Also provided are methods of determining analyte concentration.

18 Claims, 1 Drawing Sheet

U.S. PATENT DOCUMENTS

| | | | |
|---|---|---|---|
| 6,850,283 B1 * | 2/2005 | Tatamiya | 348/373 |
| 6,893,545 B2 | 5/2005 | Gotoh et al. | |
| 6,942,518 B2 | 9/2005 | Liamos et al. | |
| 2001/0017664 A1 * | 8/2001 | Misawa | 348/373 |
| 2003/0191415 A1 | 10/2003 | Moerman et al. | |
| 2004/0073095 A1 * | 4/2004 | Causey et al. | 600/300 |
| 2004/0086425 A1 * | 5/2004 | Jaunakais | 422/86 |
| 2004/0267300 A1 | 12/2004 | Mace | |
| 2005/0121826 A1 | 6/2005 | Hajizadeh et al. | |
| 2005/0154271 A1 * | 7/2005 | Rasdal et al. | 600/347 |
| 2005/0281706 A1 | 12/2005 | Funke et al. | |
| 2006/0040333 A1 * | 2/2006 | Zocchi | 435/14 |
| 2006/0148096 A1 * | 7/2006 | Jina | 436/514 |
| 2007/0100222 A1 * | 5/2007 | Mastrototaro et al. | 600/365 |
| 2007/0247793 A1 * | 10/2007 | Carnevali | 361/681 |
| 2008/0099332 A1 * | 5/2008 | Scott et al. | 204/403.01 |
| 2008/0234559 A1 * | 9/2008 | Arbogast et al. | 600/309 |

FOREIGN PATENT DOCUMENTS

| | | |
|---|---|---|
| EP | 1543935 A2 | 6/2005 |
| EP | 1712910 A1 | 10/2006 |
| WO | 2006/002432 | 1/2006 |

* cited by examiner

ANALYTE MONITORING

BACKGROUND OF THE INVENTION

Analytical sensors are commonly used to monitor the level of an analyte in a body fluid. For example, diabetics use analyte sensors to monitor body glucose levels.

Analyte testing may involve testing once per day, but typically should be carried out periodically throughout the day using multiple analyte sensors—one sensor for each test. To "read" a sensor, i.e., to analyze the body fluid applied to a sensor and determine one or more analyte levels, a sensor reader, oftentimes referred to as a "meter", is used. Either before or after a sample of body fluid is applied to a sensor, the sensor is received by a meter. The meter performs various functions and analyzes the sensor-applied sample to provide an analyte level to the user.

The sensor receiving area of a meter, commonly referred to as a sensor "port", is the opening in a meter that receives a sensor for testing. The sensor port is therefore an opening from the outside meter environment to the interior of the meter. Because the interior is exposed to the outside environment via the sensor port, the potential for contaminating materials to enter the meter's interior through the port exists. Such contamination may interfere with the readings and foul the analyte results. Given the importance of obtaining accurate analyte level readings, it is imperative that the meter does not become contaminated.

Accordingly, as analyte monitoring devices continue to be used for analyte monitoring, there continues to be an interest in methods for minimizing contamination of analyte monitoring devices, e.g., when a sensor is absent from the sensor receiving area of the device.

SUMMARY OF THE INVENTION

Analyte testing methods are provided. Embodiments include methods of minimizing contamination of a sensor port of an analyte monitoring device.

Various embodiments include covering a sensor receiving port of an analyte meter. The meter may be integrated with a continuous analyte monitoring system or not. A cover may be positioned about the meter port to provide closure thereof, and capable of being moved to a testing potion in which the port is opened so that a sensor may be received by the meter. In certain embodiments, a cover is fixedly secured at a first end to the meter, and cooperates with the meter at a second end to close the meter's port, but thereby permit rotation of the cover relative to the meter about the fixedly secured end (e.g., about a pivot point), but to substantially prevent movement of the cover relative to the meter other than to open the port for sensor access, e.g., to substantially prevent movement of the cover relative to the meter other than rotation about a pivot point at the fixed end. Accordingly, various embodiments are spring biased covers that self-close against a meter port. Embodiments of the self-closing covers may open and lock in an open position by way of a locking mechanism.

The subject invention includes methods of monitoring an analyte using the port cover. Embodiments include exposing a sensor port of a meter by moving a cover from its closed position to its open position, e.g., by moving the cover about a pivot point. Certain embodiments include moving a cover to expose a port by the action of contacting a sensor with the cover, e.g., by the action of inserting a sensor into the port of the meter.

These and various other features which characterize the invention are pointed out with particularity in the attached claims. For a better understanding of the sensors of the invention, their advantages, their use and objectives obtained by their use, reference should be made to the drawings and to the accompanying description, in which there is illustrated and described preferred embodiments of the invention.

BRIEF DESCRIPTION OF THE DRAWINGS

Referring now to the drawings, wherein like reference numerals and letters indicate corresponding structure throughout the several views.

DETAILED DESCRIPTION

Figure 1A:
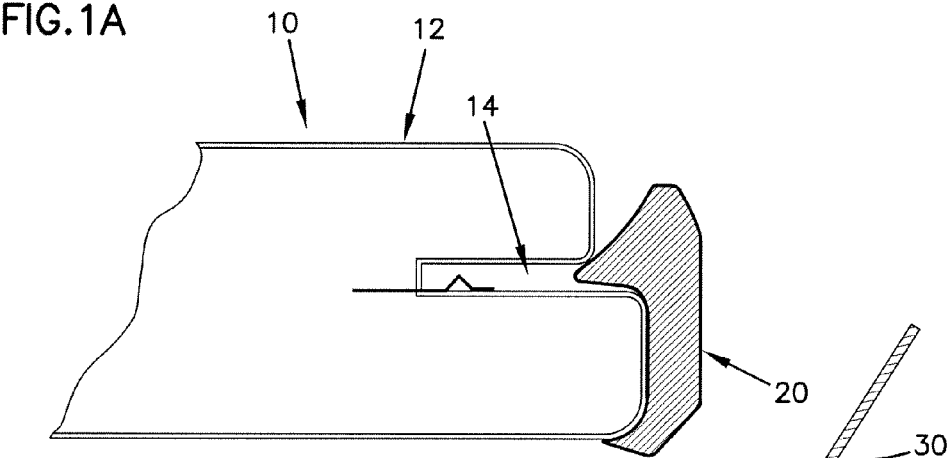
FIG. 1A shows a side view of an exemplary embodiment of a port cover in a closed position covering a sensor port of a meter.

As summarized above, methods for protecting a sensor opening or port of an analyte monitoring device are provided. The methods are particularly useful in providing openable doors to the interiors of meters to protect the interiors from contaminants that may enter the meters through the sensor ports. Accordingly, the meter doors are configured to substantially seal a sensor opening of a meter so that contaminants are excluded from the port. In certain embodiments, the port may be included in, e.g., integrated, with a continuous analyte monitoring system.

The covers may be adapted to be used with any medical device having an opening and are particularly useful as adapted to be used with an analyte monitoring medical device having an opening for receiving a sensor (also commonly referred to as a test strip), such as an in vitro analyte monitoring meter or in vivo analyte monitoring system, e.g., those provided by Abbott Diabetes Care Inc. of Alameda, Calif. Meters may be electrochemical or optical meters, and may be configured to determine the level of one or more analytes, where analytes include, but are not limited to, glucose, lactate, acetyl choline, amylase, bilirubin, cholesterol, chorionic gonadotropin, creatine kinase (e.g., CK-MB), creatine, DNA, fructosamine, glucose, glutamine, growth hormones, hormones, ketones, lactate, peroxide, prostate-specific antigen, prothrombin, RNA, thyroid stimulating hormone, and troponin, in sample of body fluid. Meters may also be configured to determine the concentration of drugs, such as, for example, antibiotics (e.g., gentamicin, vancomycin, and the like), digitoxin, digoxin, drugs of abuse, theophylline, and warfarin, may also be determined and the like, in a sample of body fluid. In certain embodiments, the covers are shaped and sized to cooperate with a FreeStyle® blood glucose monitoring meter or a Precision® brand blood monitoring meter capable of monitoring glucose and ketones. In certain embodiments, the covers may be configured to close a port of a continuous analyte monitoring system. For example, a continuous glucose monitoring system may include a component that receives analyte data from a transcutaneously inserted glucose sensor (a "receiver"), and which component may be configured to communicate analyte results to the user, e.g., audibly by way of a display, or visually. The continuous monitoring system receiver may include a conventional blood glucose meter and therefore a port for accepting a glucose test strip. The conventional meter and test strip may be used to calibrate the continuous system (see for example U.S. Pat. No. 6,175,752). It is to be understood that description of covers for opening of meters includes stand-alone meters, as well those operably connected to, e.g., integrated with, continuous analyte monitoring systems. Exemplary sensors and meters and continuous analyte monitoring systems (sometimes referred to a in vivo system) that may be employed include sensors and meters such as those described, e.g., in U.S. Pat. Nos. 6,071,391; 6,120,676; 6,143,164; 6,299,757; 6,338,790; 6,377,894; 6,600,997; 6,773,671; 6,514,460; 6,592,745; 5,628,890; 5,820,551; 6,736,957; 4,545,382; 4,711,245; 5,509,410; 6,540,891; 6,730,200; 6,764,581; 6,299,757; 6,338,790; 6,461,496; 6,503,381; 6,591,125; 6,616,819; 6,618,934; 6,676,816; 6,749,740; 6,893,545; 6,942,518; 6,175,752; and 6,514,718, and elsewhere.

The covers may be fixedly attached/attachable to a meter, or may be wholly removable from a meter. For example, a cover may be configured to be attachable to a meter over the port, but yet easily removable by a user when access to the sensor port is desired. In such cases, a cover may be removably attached about a sensor port of a meter in any suitable manner, e.g., snap fit, friction fit, hook and loop engagement (e.g., Velcro), or other chemical or physical bonding method. Alternatives include adhesive bonding, solvent welding, molded-in snap fit joints and the use of fasteners such as screws. For example, certain embodiments snap fit a soft material cover to hard plastic features (holes or slots) or injection mold into it.

In certain embodiments, a portion of a cover is attached to the meter, allowing an unattached portion to move away from the meter to expose the port. For example, a cover may be fixedly secured at its first end to a meter, and may cooperate with the meter at a second end to close the port about which the cover is positioned, yet permit movement of the cover in a direction to open the port, e.g., generally downward, upward, sideways, depending on its relation to the housing to provide access to the interior of the meter. A cover may be fixed at a portion thereof to the meter to enable rotation of the cover relative to the meter about a pivot point, e.g., about at least one hinge or spring biased hinge mechanism, but to substantially prevent movement of the cover relative to the meter other than rotation about the at least one pivot point. For example, in certain embodiments the cover is attached to the meter, e.g., at the bottom of the meter, and may be opened like a flap to expose the sensor port.

The cover may be biased in a first or closed position to cover a sensor port. In certain embodiments, a spring may bias the closeable cover in a predetermined position, for example the closed position shown in FIG. 1A. The biasing force, e.g., provided by a spring, causes the cover to swing back to its initial starting position when the force causing the initial displacement is removed, e.g., a sensor is removed from the port. By way of example, a user may open a cover by pushing or pulling on the cover, thereby causing displacement from its original position. Alternatively, insertion of a sensor into the port may provide a force sufficient to open the cover, e.g., in a single action. A sensor received in the port may maintain the cover in an open position or the cover may lock in an open position. Once the displacement force is removed, e.g., a sensor is removed from the port such as after analyte testing, the cover is urged back to its starting position to close the port.

In certain embodiments, a cover may also be configured to guide a sensor into the port. For example, a cover may include guides, rails, channels, indentions, recessed structures, elevated structures, channels, orifices, clamps, and the like, e.g., on a sensor contacting surface thereof. A cover may have two spaced apart guides extending from the cover. With this configuration, a sensor may be slid into a tested position along the guides—the action thereof causing displacement of the cover in certain embodiments. The guides may be dimensioned such that a sensor is snugly fit in the guides when it is mounted between the guides. During positioning of the sensor, portions of the sensor may be gripped (such as with a user's fingers) and the gripped portions used to then slide the sensor into the mounted position between the guides.

In certain embodiments, the covers may include a protrusion configured to at least partially enter and reside in the sensor port when in the closed position. This feature further ensures that contaminants will be kept out of the interior of the meter.

The covers may be made of any suitable material. In certain embodiments, the material is substantially flexible, but robust enough to withstand the constant movement of the covers from the closed to open positions. Elastomeric materials may be used, e.g., rubber or other compliant material. The covers may be treated or covered with a beneficial agent, e.g., antibacterial agent or the like.

The covers may be attached to the meter during manufacture, e.g., in those embodiments in which a cover is fixedly attached to a meter at least at one portion of the cover. Alternatively, a cover may be provided to users detached from a meter, but easily attachable by a user. In such instances, covers may be re-usable.

Referring now to the Figures, FIG. 1A shows an analyte meter 10 having a sensor port 12. Meter 10 includes housing 12 defining an interior space and having a sensor port 14 that is closed by sensor port cover 20. In this particular embodiment, cover 20 has a substantially C-shaped body, such that the "C" is adapted to cooperate with a portion of the meter and in particular a portion of the sensor port. Cover protrusion 26 intrudes into port 14. In this embodiment, the "C" is configured to cooperate and fit with the "bottom" of the port in a mating relationship. It will be appreciated that throughout the present application, words such as "top", "bottom", "upper", and "lower", and the like, are used in a relative sense only.

Figure 1B:
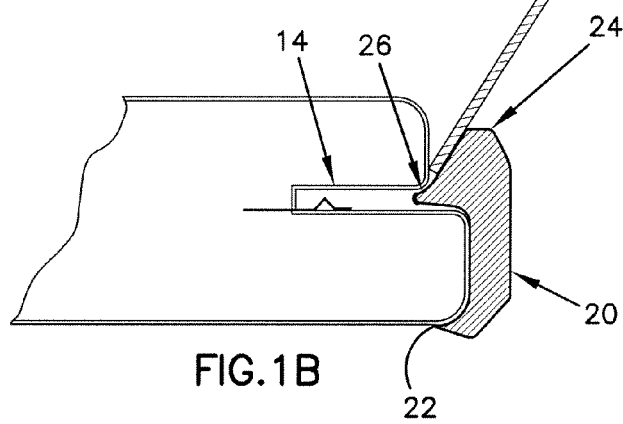
FIG. 1B shows a side view of the port cover of FIG. 1A in a closed position with a sensor positioned to be received in the port.
Figure 1C:
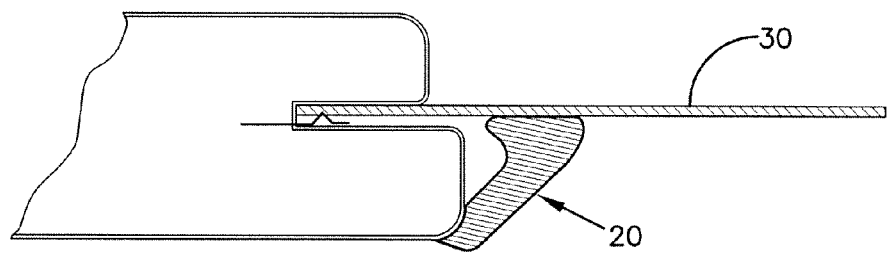
FIG. 1C shows the cover of FIGS. 1A and 1B in the open or testing position providing sensor access to the port.

FIG. 1B shows an analyte sensor 30, e.g., a glucose sensor, being positioned against cover 20 for insertion into port 14. The sensor is shown as having a generally rectangular shape, but it is to be appreciated that any shaped sensor may be used. As best seen in FIG. 1B, the bottom of the "C" or first cover end 22 is pivotally attached to the meter and the top of the "C" or second cover end 24 is not fixedly attached to the meter so that it may pivot downward as shown in FIGS. 1B and 1C. Sensor 30 is guided down a shoulder of the cover to operatively position the sensor in the sensor port. In this embodiment, the action of inserting sensor 30 into port 14 opens cover 20 to permit access to the port. This single action sensor insertion/cover opening minimizes the steps required to open the port and insert the sensor into the meter. FIG. 1C shows the cover in a fully displaced position and sensor 30 operatively positioned in port 14 for testing. Once the sensor is removed, the cover may spring back to its closed position or may be manually pushed back into position depending on the particular embodiment. When a sensor is inserted into the port, a part of the cover may contact at least a bottom (cover contacting side) and/or the sides of the sensor, to prevent sample from moving into the port along the sensor bottom side and/or one or more sensor sides. Pressure may be applied to a surface of the sensor from the cover when it is in the open position to provide a tighter cover/sensor interface.

A sample of biological fluid is provided to the sensor for analyte testing, where the level of analyte is determined. In many embodiments, it is the level of glucose in blood, interstitial fluid, and the like, that is determined. Also in many embodiments, the source of the biological fluid is a drop of blood drawn from a patient, e.g., after piercing the patient's skin with a lancing device or the like.

Embodiments of the subject methods may include contacting the sensor, either before or after opening the door to the sensor port, and transferring a volume of fluid from a skin incision to the sensor.

In any event, before, during or after sample is contacted with the sample chamber, the sensor is coupled to a meter and the concentration of an analyte in the sample, e.g., glucose, is determined.

The invention has been described with reference to various specific and preferred embodiments and techniques. However, it will be apparent to one of ordinarily skill in the art that many variations and modifications may be made while remaining within the spirit and scope of the invention.

All patents and other references in this specification are indicative of the level of ordinary skill in the art to which this invention pertains. All patents and patent applications are herein incorporated by reference to the same extent as if each individual patent was specifically and individually incorporated by reference.

We claim:

1. A method of determining the level of an analyte, the method comprising:
    opening a closed cover that is mated with a sensor port of a meter by pulling on the cover using a sensor;
    keeping the cover open using the sensor; and
    determining the level of an analyte in a sample applied to the sensor inserted into the sensor port of the meter.

2. The method of claim 1, comprising inserting the sensor into the sensor port to open the closed cover.

3. The method of claim 1, comprising determining the analyte electrochemically.

4. The method of claim 1, comprising determining the analyte optically.

5. The method of claim 1, wherein the analyte is glucose.

6. The method of claim 1, wherein the meter is a glucose meter.

7. The method of claim 1, wherein the port is integrated with a continuous analyte monitoring system.

8. The method of claim 7, further comprising calibrating the continuous analyte monitoring system using the determined level of analyte.

9. The method of claim 1, wherein the method further comprises closing the sensor port by biasing a sensor cover in a closed mated position about the sensor port opening of the meter by removing the sensor that is keeping the sensor cover in an open position from the sensor port.

10. A method for calibrating a continuous glucose monitoring system having a glucose test strip port integrated with the system, the method comprising:
    opening a closed cover mated with the port to expose the port to receive a test strip by pulling on the cover using the test strip;
    keeping the cover open using the test strip;
    determining the concentration of an analyte from the test strip inserted into the port; and
    calibrating the continuous analyte system with the determined analyte concentration.

11. The method of claim 10, wherein the opening comprises moving the cover from a first position wherein the cover closes the port to a second position that provides the test strip access to the port.

12. The method of claim 11, wherein the second position is provided by moving a portion of the cover away from the port while another portion of the cover remains attached.

13. The method of claim 12, wherein the attached portion is fixedly attached.

14. The method of claim 12, wherein the attached portion is pivotally attached.

15. The method of claim 10, comprising contacting the cover with a test strip received in the port.

16. The method of claim 15, comprising applying pressure against a test strip received in the port with the cover.

17. The method of claim 1, wherein the cover comprises an elastomeric material.

18. The method of claim 1, wherein the cover comprises a protrusion configured to at least partially enter and reside in the sensor port.

* * * * *